(12) United States Patent
Kim et al.

(10) Patent No.: US 11,028,026 B2
(45) Date of Patent: Jun. 8, 2021

(54) REACTOR FOR NON-OXIDATIVE DIRECT CONVERSION OF METHANE AND METHOD OF MANUFACTURING ETHYLENE AND AROMATIC COMPOUND USING SAME

(71) Applicant: KOREA RESEARCH INSTITUTE OF CHEMICAL TECHNOLOGY, Daejeon (KR)

(72) Inventors: Yong Tae Kim, Daejeon (KR); Sung Woo Lee, Daejeon (KR); Seung Ju Han, Daejeon (KR); Seok Ki Kim, Daejeon (KR); Hyun Woo Kim, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/667,936

(22) Filed: Oct. 30, 2019

(65) Prior Publication Data

US 2020/0354290 A1 Nov. 12, 2020

(30) Foreign Application Priority Data

Jan. 31, 2019 (KR) .................. 10-2019-0012688

(51) Int. Cl.
*B01J 19/24* (2006.01)
*C07C 2/76* (2006.01)
(Continued)

(52) U.S. Cl.
CPC ............ *C07C 5/415* (2013.01); *B01J 15/005* (2013.01); *B01J 19/242* (2013.01);
(Continued)

(58) Field of Classification Search
None
See application file for complete search history.

(56) References Cited

U.S. PATENT DOCUMENTS

| 4,424,401 A | 1/1984 | White et al. |
| 8,013,196 B2 | 9/2011 | Mamedov et al. |

(Continued)

FOREIGN PATENT DOCUMENTS

| EP | 1707549 A1 * | 10/2006 | ............... C07C 5/09 |
| WO | WO-0170656 A1 * | 9/2001 | ............. C10G 15/08 |

OTHER PUBLICATIONS

Xiaoguang Guo et al, Direct, Nonoxidative Conversion of Methane to Ethylene, Aromatics, and Hydrogen, Science, May 9, 2017, pp. 616-619, vol. 344, American Association for the Advancement of Science, Washington DC, USA.

(Continued)

*Primary Examiner* — Jennifer A Leung
(74) *Attorney, Agent, or Firm* — STIP Law Group, LLC

(57) ABSTRACT

The present invention relates to a reactor for non-oxidative direct conversion of methane and a method of manufacturing ethylene and an aromatic compound using the same. More particularly, the present invention relates to a reactor for non-oxidative direct conversion of methane in which a catalytic reaction velocity is maximized, the production of coke is minimized, and a high conversion rate of methane and a high yield of ethylene and an aromatic compound are ensured when ethylene and the aromatic compound are manufactured from methane, and a method of manufacturing ethylene and an aromatic compound using the same.

10 Claims, 2 Drawing Sheets

(51) Int. Cl.
*C07C 5/09* (2006.01)
*C07C 2/48* (2006.01)
*C07C 5/41* (2006.01)
*C07C 5/333* (2006.01)
*B01J 15/00* (2006.01)
*B01J 35/02* (2006.01)
*B01J 23/889* (2006.01)
*B01J 35/00* (2006.01)
*B01J 27/24* (2006.01)

(52) U.S. Cl.
CPC ........... *B01J 23/8898* (2013.01); *B01J 27/24* (2013.01); *B01J 35/0006* (2013.01); *B01J 35/02* (2013.01); *C07C 2/48* (2013.01); *C07C 2/76* (2013.01); *C07C 5/09* (2013.01); *C07C 5/3335* (2013.01); *C07C 2523/26* (2013.01); *C07C 2523/28* (2013.01); *C07C 2523/34* (2013.01); *C07C 2523/745* (2013.01); *C07C 2523/75* (2013.01); *C07C 2523/755* (2013.01)

(56) References Cited

U.S. PATENT DOCUMENTS 9,327,265 B2 * 5/2016 Bricker .................... C07C 2/82
2013/0136687 A1 * 5/2013 Darr ..................... B01J 19/0093
423/592.1
2016/0362351 A1 12/2016 Nagaki et al.
2018/0296974 A1 10/2018 Wachsman et al.

OTHER PUBLICATIONS

Mann Sakbodin et al, Hydrogen-Permeable Tubular Membrane Reactor: Promoting Conversion and Product Selectivity for Non-oxidative Activation of Methane over an FeVSiO2 Catalyst, Angewandte Chemie,. 2016, pp. 16383-16386, vol. 128, Wiley-VCH Verlag GmbH & Co, KGaA, Weinheim, Germany.

* cited by examiner

REACTOR FOR NON-OXIDATIVE DIRECT CONVERSION OF METHANE AND METHOD OF MANUFACTURING ETHYLENE AND AROMATIC COMPOUND USING SAME

CROSS REFERENCE TO RELATED APPLICATION

The present application claims priority based on Korean Patent Application No. 10-2019-0012688, filed on Jan. 31, 2019, the entire content of which is incorporated herein for all purposes by this reference.

BACKGROUND OF THE INVENTION

1. Field of the Invention

The present invention relates to a reactor for non-oxidative direct conversion of methane and a method of manufacturing ethylene and an aromatic compound using the same. More particularly, the present invention relates to a reactor for non-oxidative direct conversion of methane, which is used to directly convert methane, which is a main component of natural gas, in an anaerobic or anoxic atmosphere to thus manufacture ethylene and an aromatic compound, and to a method of manufacturing ethylene and an aromatic compound using the same.

2. Description of the Related Art

Recently, continuous efforts have been made to convert methane ($CH_4$), which is capable of being obtained from natural gas and shale gas, into high-value-added products such as transportation fuels or chemical raw materials. Representative examples of high-value-added products capable of being obtained from methane may include olefins (ethylene, propylene, butylene, etc.) and aromatic compounds. MTO (Methanol-to-Olefin) technology for manufacturing light olefins via methanol from synthetic gas ($H_2$+CO) obtained through methane reformation and FTO (Fischer-Tropsch-to-Olefin) technology for directly producing light olefins from synthetic gas are the most feasible known technologies. However, the above-described technologies for producing high-value-added products using synthetic gas require additional $H_2$ or CO in order to remove 0 atoms from CO, which reduces the utilization efficiency of H or C atoms in the entire process.

Therefore, there is a need for a new technology for directly converting methane into high-value-added products without using synthetic gas. In order to directly convert methane into high-value-added products, first of all, methane needs to be activated by cleaving the strong C—H bond (434 kJ/mol) formed in methane. With respect thereto, research on a methane-coupling reaction (Oxidative Coupling of Methane; OCM) technology for activating methane using oxygen has been actively performed. However, it is still noted as a problem that even in the OCM reaction, due to the intense reactivity of $O_2$, a large amount of thermodynamically stable $H_2O$ and $CO_2$ is formed, thereby reducing the utilization efficiency of H or C atoms.

In order to overcome this problem, technology for manufacturing ethylene and an aromatic compound by direct conversion of methane under anaerobic or anoxic conditions has been recently developed. The technology is embodied at high temperature under high pressure due to the low reactivity of methane, and the development of reactors and catalysts suitable for the technology is essential. However, according to the results of research to date, the problem of a sudden decrease in catalyst activity due to the deposition of carbon (coke) on the catalyst under high-temperature and high-pressure conditions is emerging as a key issue (see Non-Patent Documents 0001 and 0002).

Accordingly, U.S. Pat. No. 4,424,401 discloses a method of diluting acetylene using an inert gas, water, hydrogen, methane, and alcohol in the presence of a zeolite catalyst ZSM-5, thus performing aromatization into a hydrocarbon mixture. U.S. Pat. No. 8,013,196 discloses a method of pyrolyzing a feed containing methane so that the feed is thermally converted into a discharged material containing acetylene, and then hydrogenating the discharged material containing acetylene obtained using the conversion, thus manufacturing ethylene.

However, the aromatization method of methane or acetylene on zeolites or other catalysts as disclosed in these prior-art documents has problems in that the accumulation of coke fragments and the rapid polymerization of acetylene result in a very short time period of catalyst performance and rapid deactivation thereof. Moreover, large amounts of other byproducts are formed due to the acetylene conversion.

In particular, a known method of producing ethylene and an aromatic compound from a methane-containing feed has some drawbacks such as the deactivation of catalysts, excessive hydrogenation, the formation of green oil or carbon, an excessively high temperature, or low productivity per unit volume of the reactor.

Therefore, there is a need in the related art for the development of techniques for improved methods and reactors that allow for more efficient and stable manufacture of aromatic compounds and ethylene from methane, in particular.

PRIOR ART DOCUMENT

Patent Document (Patent Document 0001) U.S. Pat. No. 4,424,401 (Registration Date: 1984 Jan. 3)
(Patent Document 0002) U.S. Pat. No. 8,013,196 (Registration Date: 2011 Sep. 6)

Non-Patent Document (Non-Patent Document 0001) X, Guo et al., Direct, Non-oxidative Conversion of Methane to Ethylene, Aromatics, and Hydrogen, Science, 344, 2014, 616~619
(Non-Patent Document 0002) Mann Sakbodin et al., Hydrogen-Permeable Tubular Membrane Reactor: Promoting Conversion and Product Selectivity for Non-oxidative Activation of Methane over an FeVSiO2 Catalyst, Angew. Chem. 2016, 128, 16383~16386

SUMMARY OF THE INVENTION

Accordingly, the present invention has been made keeping in mind the above problems occurring in the related art, and a main object of the present invention is to provide a reactor for non-oxidative direct conversion of methane, in which a catalytic reaction velocity is maximized, the production of coke is minimized, and a high conversion rate of methane and a high yield of ethylene and an aromatic compound are ensured when ethylene and the aromatic compound are manufactured from methane, and a method of manufacturing ethylene and an aromatic compound using the same.

In order to accomplish the above object, an embodiment of the present invention provides a reactor for the non-oxidative direct conversion of methane. The reactor includes an introduction unit for introducing a methane-containing feed, a reaction unit for reacting the methane-containing feed introduced through the introduction unit to produce a product containing ethylene and an aromatic compound, and a discharge unit for discharging the product containing the ethylene and the aromatic compound produced in the reaction unit. The reaction unit includes a first reaction region unit, for reacting the methane-containing feed introduced through the introduction unit to produce acetylene, and a second reaction region unit, for hydrogenating the acetylene produced in the first reaction region unit to produce the ethylene and the aromatic compound, and the second reaction region unit is provided with a hydrogen supply tube which is coaxially disposed in the reactor and which is hollow so that hydrogen is supplied from the discharge unit to the introduction unit through the hollow hydrogen supply tube.

In a preferable embodiment of the present invention, the reactor for non-oxidative direct conversion of methane may include a second reaction region catalyst in a reactor inner circumferential surface or the hydrogen supply tube of the second reaction region unit.

In the preferable embodiment of the present invention, the second reaction region catalyst may include one or more selected from the group consisting of iron, chromium, nickel, molybdenum, and manganese.

In the preferable embodiment of the present invention, a ratio of a mean residence time in the second reaction region unit to a mean residence time in the first reaction region unit in the reactor for non-oxidative direct conversion of methane may range from 0.01 to 1.5.

In the preferable embodiment of the present invention, a ratio of a superficial velocity in the second reaction region unit to a superficial velocity in the first reaction region unit in the reactor for non-oxidative direct conversion of methane may be 1 to 30.

In the preferable embodiment of the present invention, a space velocity of the second reaction region unit may be 800 to 20,000 $cm^3$ $gcat^{-1}$ $h^{-1}$.

In the preferable embodiment of the present invention, a reaction may be performed at 900 to 2,000° C. under 0.1 to 10 bar in the first reaction region unit.

In the preferable embodiment of the present invention, the hydrogenating may be performed at 500 to 1,300° C. under 0.1 to 10 bar in the second reaction region unit.

In the preferable embodiment of the present invention, a reactor inner circumferential surface of the first reaction region unit may be coated with a first reaction catalyst containing $Si_xN_yO_z$ (x=1 to 3, y=4 or less, z=2 or less).

In the preferable embodiment of the present invention, a ratio of a surface area of the second reaction region catalyst to a reactor volume of the second reaction region unit may be 1 to 10 $cm^{-1}$.

Another embodiment of the present invention provides a method of manufacturing ethylene and an aromatic compound from methane using the reactor for non-oxidative direct conversion of methane.

According to the present invention, it is possible to maximize a catalytic reaction velocity, to minimize the production of coke, and to ensure a high conversion rate of methane and a high yield of ethylene and an aromatic compound when ethylene and the aromatic compound are manufactured from methane.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
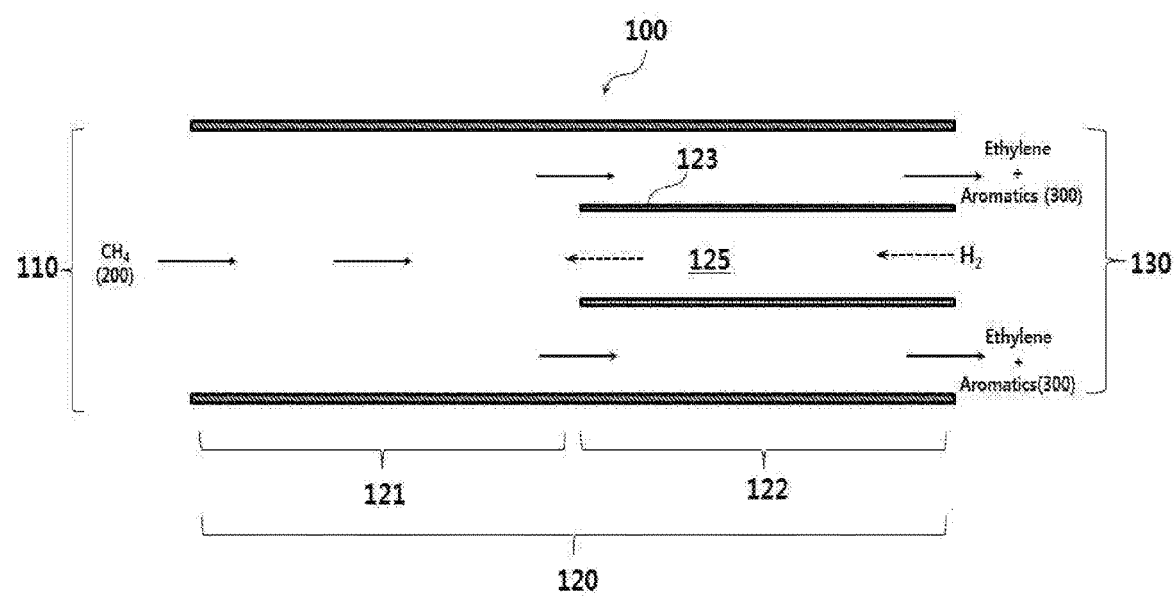
FIG. 1 is a schematic view showing the longitudinal section of a reactor for non-oxidative direct conversion of methane according to an embodiment of the present invention.

Unless defined otherwise, all technical and scientific terms used in the present specification have the same meanings as those commonly understood by one of ordinary skill in the art to which the present invention belongs. In general, the nomenclature used in the present specification is well known and commonly used in the art.

When a part is said to "include" a certain component throughout the present specification, it means that it may further include other components, and does not necessarily exclude other components unless specifically stated otherwise.

Terms such as "comprise", "include", or "have" as used in the present specification refer to the presence of features, numerical values, steps, operations, components, parts, or combinations thereof described in the specification, and do not exclude the possibility that other features, numerical values, steps, operations, components, parts, or combinations thereof not mentioned herein may be present or added.

Throughout the present specification, "reaction unit" or "reaction region" means the space in the reactor where the reactants react. "Inner" and "inside" mean facing the radial center of the circle, which is the shape of a cross section of the reactor obtained by cutting the reactor perpendicularly with respect to the direction of gravity. "Outer" and "outside" mean facing the radial circumference of the circle, which is the shape of a cross section of the reactor obtained by cutting the reactor perpendicularly with respect to the direction of gravity.

Further, throughout the present specification, the names of the configurations are divided into "first", "second", and the like in order to clearly describe the configurations for the purpose of distinguishing configurations having the same name, and do not necessarily limit the order in the following description.

An aspect of the present invention relates to a reactor for non-oxidative direct conversion of methane. The reactor includes an introduction unit for introducing a methane-containing feed, a reaction unit for reacting the methane-containing feed introduced through the introduction unit to produce a product containing ethylene and an aromatic compound, and a discharge unit for discharging the product containing the ethylene and the aromatic compound produced in the reaction unit. The reaction unit includes a first reaction region unit for producing acetylene using the methane-containing feed introduced through the introduction unit and a second reaction region unit for hydrogenating the acetylene produced in the first reaction region unit to produce the ethylene and the aromatic compound. The second reaction region unit is provided with a hydrogen supply tube which is coaxially disposed in the reactor and is hollow so that hydrogen is supplied from the discharge unit to the introduction unit through the hollow hydrogen supply tube.

More specifically, when the ethylene and the aromatic compound are manufactured from methane, examples of main factors for inducing the production of coke include the surface of the catalyst cluster charged in the reactor, the stagnant flow of fluid, the material of the reactor, and the surface of the reactor (reactor roughness).

Accordingly, in the present invention, the reaction unit of the reactor for non-oxidative direct conversion of methane is divided into the first reaction region unit and the second reaction region unit. In the second reaction region unit, the hydrogen supply tube, through which hydrogen is supplied, is disposed coaxially with the reactor. The inside of the reactor is not filled with the catalyst by charging, but the inner wall of the reactor or the hydrogen supply tube is coated with the catalyst or includes the catalyst, which ensures a constitution that stabilizes the inner wall of the reactor and is very useful for forming laminar flow of reactants and products. Further, the mean residence time, the superficial velocity, and the space velocity (WHSV) of the first reaction region unit and the second reaction region unit may be adjusted, thus maximizing the catalytic reaction velocity, minimizing the production of coke, and ensuring a high conversion rate of methane and a high yield of ethylene and an aromatic compound.

Hereinafter, the present invention will be described in detail with reference to the accompanying drawings.

Figure 2:
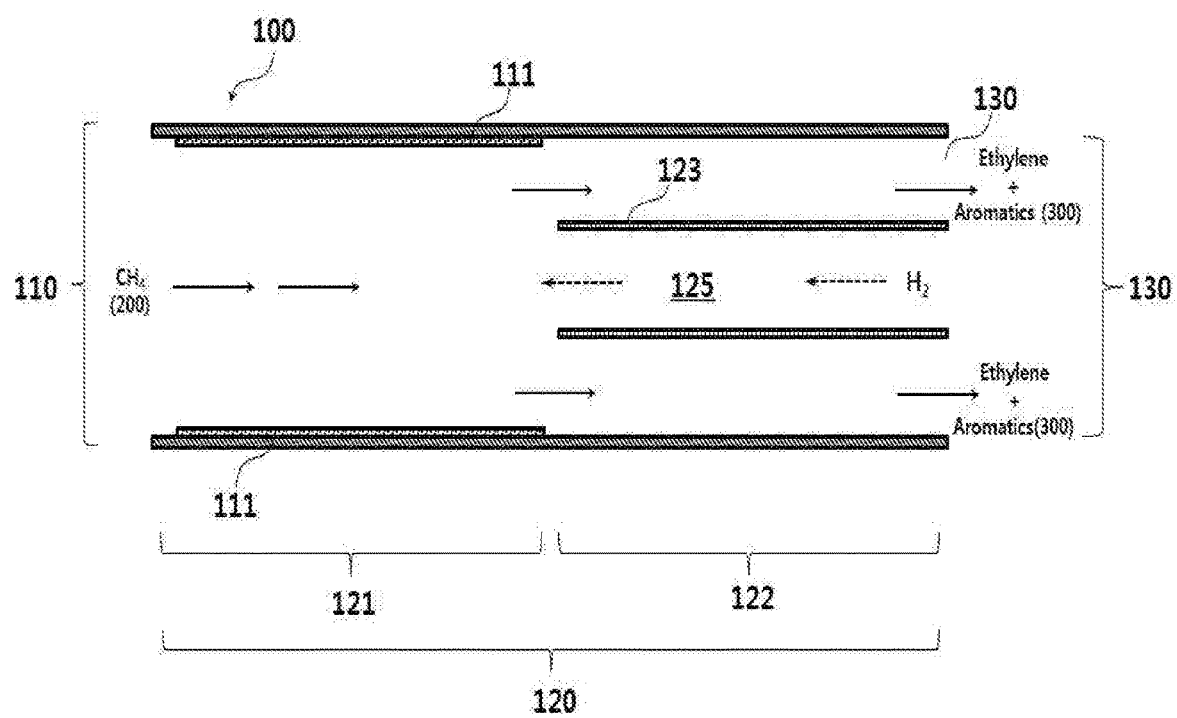
FIG. 2 is a schematic view showing the longitudinal section of a reactor for non-oxidative direct conversion of methane according to another embodiment of the present invention.

FIG. 1 is a schematic view showing the longitudinal section of a reactor for non-oxidative direct conversion of methane according to an embodiment of the present invention. FIG. 2 is a schematic view showing the longitudinal section of a reactor for non-oxidative direct conversion of methane according to another embodiment of the present invention.

A reactor 100 for non-oxidative direct conversion of methane according to the present invention includes an introduction unit 110 for introducing a methane-containing feed 200, a reaction unit 120 for reacting the methane-containing feed introduced through the introduction unit 110 to produce a product 300 containing ethylene and an aromatic compound, and a discharge unit 130 for discharging the product 300 containing the ethylene and the aromatic compound produced in the reaction unit 120.

The reactor 100 may vary in dimensions or shape depending on a production capacity, a supply amount, and a catalyst, and the dimensions or shape may be adjusted using various methods known to those skilled in the art. Preferably, the reactor is a tubular reactor, and the introduction unit 110 is formed at one side thereof to introduce the methane-containing feed 200 therethrough. The introduced methane-containing feed 200 is reacted in the reaction unit 120, and the discharge unit 130 is formed at a side opposite the introduction unit, thus discharging the product 300 containing the ethylene and the aromatic compound to the outside or the rear end thereof after the completion of the reaction.

The introduction unit 110 of the reactor may be disposed in the reactor at any side of an upper side, a lower side, a right side, or a left side thereof. Further, the discharge unit 130 may be disposed at the side opposite the introduction unit so as to correspond in position to the introduction unit.

As the methane-containing feed 200 introduced into the introduction unit 110, any composition may be used without limitation, as long as it is a composition that contains methane. The feed may contain, for example, natural gas, and preferably inert gas and/or non-inert gas in addition to methane.

The amount of the methane contained in the methane-containing feed may be 2% or more (v/v) and more preferably 40 to 100% (v/v) based on the total volume of the methane-containing feed supplied into the reactor. The amount of the inert gas and/or non-inert gas may be 98% or less (v/v), and more preferably 60% or less (v/v), based on the total volume of the methane-containing feed.

The inert gas and/or non-inert gas serve to stably generate and maintain a reaction state. The inert gas may be nitrogen, helium, neon, argon, or krypton, and the non-inert gas may be carbon monoxide, hydrogen, carbon dioxide, water, monohydric alcohol (carbon number of 1 to 5), dihydric alcohol (carbon number of 2 to 5), or alkanes (carbon number of 2 to 8). Preferably, the inert gas and the non-inert gas may be nitrogen, hydrogen, oxygen, or water.

The methane-containing feed introduced through the introduction unit 110 into the reaction unit 120 passes through a first reaction region unit 121 and a second reaction region unit 122 to produce the product 300 containing the ethylene and the aromatic compound.

In the first reaction region unit 121, the introduced methane-containing feed is subjected to pyrolysis or a non-oxidative-direct-conversion reaction of methane, thus producing acetylene as in the following Reaction Equation 1.

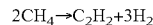

$$2CH_4 \rightarrow C_2H_2 + 3H_2 \qquad \text{[Reaction Formula 1]}$$

The reaction in the first reaction region unit 121 may be performed at 900 to 2,000° C., and preferably at 950 to 1,300° C., under 0.1 to 10 bar, and preferably under 0.1 to 5 bar.

The above-described reaction condition range is set in consideration of the selectivity and yield of hydrocarbon, and is useful in maximizing the selectivity of the methane to the hydrocarbon. That is, the production of coke may be minimized under the above conditions, thus minimizing the pressure drop caused by the production of coke and the carbon efficiency according to the production of coke during the reaction.

When the reaction temperature in the first reaction region unit 121 is less than 900° C., since the radical production rate is low due to the activation of methane, energy efficiency is low. When the reaction temperature is more than 2,000° C., it is necessary to minimize the residence time of methane in the reactor in order to suppress the production of coke, and a problem occurs in that it takes a lot of energy to heat the reactor.

Further, when the reaction pressure in the first reaction region unit 121 is less than 0.1 bar, the production of coke may be suppressed, but energy efficiency is low due to the low activation of methane. When the reaction pressure is more than 5 bar, since the production of coke is promoted, a problem may arise in that design with regard to the reactor residence time and the cooling of products must be carefully performed.

Meanwhile, in the first reaction region unit 121, the inner wall (inner circumferential surface) of the reactor may be coated with a first reaction catalyst 111, which may promote the acetylation of methane, thus forming a catalyst layer, as shown in FIG. 2. The first reaction catalyst 111 has a structure in which the inner circumferential surface of the reactor is coated with the catalyst instead of a catalyst-filled structure. The first reaction catalyst is very useful in forming a laminar flow and may serve to overcome the stagnant flow of reactants and products. Accordingly, it is possible to suppress the production of crystalline coke caused by the progression of further reactions upon the activation of methane.

The first reaction catalyst 111 includes $Si_xN_yO_z$ (x=1 to 3, y=4 or less, z=2 or less), and may further include one or more selected from the group consisting of iron (Fe), copper (Cu), manganese (Mn), cobalt (Co), nickel (Ni), zinc (Zn), aluminum (Al), sodium (Na), chromium (Cr), and potassium (K). Alternatively, the above components may be included in the first reaction catalyst while contained in a carrier such as silica, titania, zirconia, silicon carbide, boron nitride, alumina nitride, alumina, aluminum nitride silica, and magnesia.

As described above, acetylene is produced from the methane-containing feed due to the reaction in the first reaction region unit 121, and is then introduced into the second reaction region unit 122. The acetylene-containing reactant introduced into the second reaction region unit 122 is hydrogenated using hydrogen supplied from a hydrogen supply tube 125 to thus synthesize ethylene and an aromatic compound, as shown in Reaction Equation 2 below.

$$C_2H_2 + H_2 \rightarrow C_2H_4$$

$$3C_2H_2 \rightarrow C_6H_6$$

$$5C_2H_2 \rightarrow C_{10}H_8 + H_2 \qquad \text{[Reaction Formula 2]}$$

The hydrogenating in the second reaction region unit 122 may be performed at 500 to 1,300° C., and preferably 700 to 1,100° C., under 0.1 to 10 bar, and preferably 0.1 to 5 bar. The space velocity of the second reaction region unit may be 800 to 20,000 $cm^3$ $gcat^{-1}$ $h^{-1}$, and preferably 2,000 to 18,000 $cm^3$ $gcat^{-1}$ $h^{-1}$, and the mean residence time of the second reaction region unit may be 0.005 to 0.1 minutes.

The above-described reaction conditions are set in consideration of the selectivity and yield of hydrocarbon, and are useful in maximizing the selectivity of acetylene to the hydrocarbon. That is, the production of coke may be minimized under the above conditions, thus minimizing the pressure drop and the deposition of carbon caused by the production of coke during the reaction.

When the reaction temperature in the second reaction region unit 122 is less than 500° C., since the reactivity of acetylene is low, the reactor size of the second reaction region unit 122 to that of the first reaction region unit 121 may be increased. When the reaction temperature is more than 1,300° C., acetylene side reactions (dehydrogenation and coupling) may be predominant, resulting in a problem of increased production of coke.

Further, when the reaction pressure in the second reaction region unit 122 is less than 0.1 bar, since the reactivity of acetylene is low, the reactor size of the second reaction region unit to that of the first reaction region unit 121 may be increased. When the reaction pressure is more than 10 bar, side reactions (dehydrogenation and coupling) of acetylene may be predominant, resulting in a problem of increased production of coke.

Further, when the space velocity (weight hourly space velocity, WHSV) in the second reaction region 122 is less than 800 $cm^3$ $gcat^{-1}$ $h^{-1}$ or when the mean residence time is more than 0.1 minutes, the production of coke may be promoted. When the space velocity is more than 20,000 $cm^3$ $gcat^{-1}$ $h^{-1}$ or when the mean residence time is less than 0.005 minutes, since the reactivity of acetylene is low, the reactor size of the second reaction region unit relative to that of the first reaction region unit may need to be increased.

In the second reaction region unit 122, the reactor inner circumferential surface (inner wall) or the hydrogen supply tube of the second reaction region unit is coated with the second reaction region catalyst 123 for promoting the aromatization of acetylene, or the reactor inner circumferential surface (inner wall) or the hydrogen supply tube contains the second reaction region catalyst 123 for the purpose of mounting on the reactor. This is very useful for the formation of laminar flow of reactants and products, mitigates the stagnant flow of the reactants and products, and suppresses the production of crystalline coke due to the strong adsorption of the reactants on the surface of the catalyst cluster. With respect to the application of the second reaction region catalyst 123 on the hydrogen supply tube, preferably, the outer circumferential surface (outer wall) of the hydrogen supply tube may be coated with the second reaction region catalyst.

As the second reaction region catalyst, any catalyst may be applied without limitation, as long as it is a catalyst capable of promoting the aromatization of acetylene. Preferably, the second reaction region catalyst may contain at least one of iron, chromium, nickel, molybdenum, and manganese. More preferably, the content of iron among the above components may be 0.1 wt % or more based on the total weight of the catalyst.

The hydrogen supply tube 125 is a member for supplying hydrogen in order to hydrogenate the acetylene produced in the first reaction region unit 121. The hydrogen supply tube may be disposed coaxially and parallel to the inside of the reactor of the second reaction region unit, and may be hollow so that hydrogen is supplied from the discharge unit 130 to the introduction unit 110 through the hollow hydrogen supply tube, whereby the stagnant flow of the products produced in the first reaction region unit and the reactants may be avoided, thereby suppressing the production of crystalline coke.

The size, dimensions, or shape of the hydrogen supply tube 125 may vary depending on the reactor size, the supply amount, and the catalyst. The number of hydrogen supply tubes provided in the reactor may be adjusted depending on the reactor size, but an increase in the number of hydrogen supply tubes may cause stagnant flow of the reactants. Accordingly, the number of hydrogen supply tubes may be preferably one or more, and more preferably one to five, so as to prevent the production of coke.

Further, the ratio of the surface area of the second reaction region catalyst to the reactor volume of the second reaction region unit (the surface area of the second reaction region catalyst/the reactor volume of the second reaction region unit) may be 1 to 10 $cm^{-1}$. For example, when a cylinder reactor is used and when the hydrogen supply tube including the second reaction region catalyst is provided in the second reaction region unit of the reactor, the ratio of the surface area of the second reaction region catalyst to the reactor volume of the second reaction region unit may be represented by the following Equation 1.

$$(2 \times r \times n)/R^2 = 1 \text{ cm}^{-1} \sim 10 \text{ cm}^{-1} \qquad \text{[Equation 1]}$$

r is the radius of the hydrogen supply tube, R is the reactor radius of the second reaction region unit, n is the number of hydrogen supply tubes, and L means the length of the hydrogen supply tube. Accordingly, the reactor volume of the second reaction region unit may be represented by $R^2 \times L \times n$, and the surface area of the second reaction region catalyst may be represented by $2\pi \times r \times L \times n$.

When the surface area of the second reaction region catalyst to the reactor volume of the second reaction region unit is less than 1 cm$^{-1}$, there may be a problem in that the reactivity of acetylene is low and thus the reactor size of the second reaction region unit may need to be larger than that of the first reaction region unit. When the surface area of the second reaction region catalyst to the reactor volume of the second reaction region unit is more than 10 cm$^{-1}$, the product induced from acetylene may be re-adsorbed, resulting in a problem of increasing the selectivity of coke.

Meanwhile, in the reactor 100 for non-oxidative direct conversion of methane according to the present invention, the ratio of the mean residence time in the second reaction region unit to the mean residence time in the first reaction region unit described above may be 0.01 to 1.5, and preferably 0.04 to 1.0.

When the ratio of the mean residence time in the second reaction region unit to the mean residence time in the first reaction region unit is less than 0.01, there may be a problem in that acetylene is contained in the product due to the low reactivity of acetylene. When the mean residence time ratio is more than 1.5, the reactor size of the second reaction region unit relative to that of the first reaction region unit may need to be increased, resulting in a problem of reduced thermal efficiency.

Further, in the reactor 100 for non-oxidative direct conversion of methane according to the present invention, the ratio of the superficial velocity in the second reaction region unit to the superficial velocity in the first reaction region unit described above may be 1 to 30, and preferably 3 to 20.

When the ratio of the superficial velocity in the second reaction region unit to the superficial velocity in the first reaction region unit is less than 1, the product induced from acetylene in the second reaction region unit may be re-adsorbed, resulting in a problem of increasing the selectivity of coke. When the superficial velocity ratio is more than 30, the reactivity of acetylene is reduced and the reactor diameter ratio is increased, which may cause a difficulty in the design of the reactor.

The product containing the ethylene and the aromatic compound thus synthesized is discharged to the outer circumference or the rear end through the discharge unit 130 of the reactor.

In another aspect, the present invention relates to a method of manufacturing ethylene and an aromatic compound from methane using the reactor for non-oxidative direct conversion of methane.

In the method of manufacturing the ethylene and the aromatic compound according to the present invention, when the methane-containing feed 200 is supplied through the introduction unit 110 of the reactor 100 for non-oxidative direct conversion of methane, acetylene is produced due to the reaction in the first reaction region unit 121 of the reactor, the produced acetylene is introduced into the second reaction region unit 122, and the acetylene introduced into the second reaction region unit 122 is hydrogenated with hydrogen supplied through the hydrogen supply tube 125, whereby the ethylene and the aromatic compound are manufactured and then discharged through the discharge unit 130.

The description of the method of manufacturing the ethylene and the aromatic compound according to the present invention is the same as the content mentioned in the corresponding reactor for non-oxidative direct conversion of methane, so a person skilled in the art will be able to clearly understand the above-described manufacturing method. Accordingly, the description of the method will be omitted in order to avoid duplication of the description.

Hereinafter, the present invention will be described in more detail with reference to specific Examples. The following Examples are merely examples to help understanding of the present invention, but the scope of the present invention is not limited thereto.

Examples 1 and 2

Ethylene and an aromatic compound were manufactured from methane using the reactor for non-oxidative direct conversion of methane as shown in FIG. 1, and a quartz-tube reactor (inner diameter: 7 mm) was used as the above-described reactor. A hydrogen supply tube in a second reaction region unit was obtained by shaping a second reaction region catalyst having a compositional ratio of $Ni_{11}Cr_{18}Mo_{2.5}Fe_{66.5}C_{0.08}Mn_{2.0}$ into a tube (inner diameter: 0.74 mm), and was mounted on the second reaction region unit of the reactor. The surface area of the second reaction region catalyst to the reactor volume of the second reaction region unit was 1.2 cm$^{-1}$. As the methane-containing feed introduce into the reactor, 45% (v/v) of methane, 50% (v/v) of hydrogen, and 5% (v/v) of argon were mixed and then used. In the second reaction region unit, hydrogen was supplied through the hydrogen supply tube, and the reaction was performed under the conditions described in Table 1. The argon used in this case was used as an internal standard for analysis.

Subsequently, gaseous hydrocarbons of the obtained product were analyzed using a Series 6500 GC from YL Instrument Company. The gaseous product was analyzed using a thermal conductivity detector (TCD) connected to a ShinCarbon ST column and two flame ionization detectors (FID) connected to Rt-alumina BOND and RTx-VMS columns. $He_2$, $CH_4$, and CO were separated from the ShinCarbon ST column and then detected using the TCD. The conversion rate was calculated using the ratio of the area of $CH_4$ to the area of Ar, which is an internal standard. Light hydrocarbons in the range of $C_1$ to $C_5$ were separated using the Rt-alumina BOND column and then detected using the FID. The aromatic compound was separated using the RTx-VMS column and then detected using the FID. A carbon balance was maintained at 98% or more through the detection of the unreacted gases and product. All gases were quantified using a standard sample. The selectivity of coke was calculated using [Scoke=100–Σ selectivity of product]. The composition of the product thus measured is shown in Table 2.

Example 3

Ethylene and an aromatic compound were manufactured from methane using the reactor for non-oxidative direct conversion of methane as shown in FIG. 2. The first reaction catalyst in the first reaction region unit was coated with 0.33 g of polysilazane mixed with 0.2 g of Fe@SiO$_2$, and was heat-treated at 800° C., thus forming a Si$_2$N$_2$O catalyst layer containing Fe@SiO$_2$. A hydrogen supply tube in a second reaction region unit was obtained by shaping a second reaction region catalyst having a compositional ratio of $Ni_{11}Cr_{18}Mo_{2.5}Fe_{66.5}C_{0.08}Mn_{2.0}$ into a tube (inner diameter: 0.74 mm), and was mounted on the second reaction region unit. The Fe@SiO$_2$ was manufactured using the method disclosed in U.S. Laid-Open Patent Application No. 2014-0336432. The reaction was performed under the conditions shown in Table 1. The product was measured in the same manner as in Example 1, and the composition thereof is shown in Table 2.

TABLE 1

|  | Classification | Example 1 | Example 2 | Example 3 |
|---|---|---|---|---|
| First reaction region unit | Reaction temperature (° C.) | 1114 | 1082 | 1102 |
|  | Reaction pressure (bar) | 1 | 1 | 1 |
|  | Methane-containing feed: 45% (v/v) $CH_4$ + 50% (v/v) $H_2$ ($cm^3 min^{-1}$) | 40 | 40 | 40 |
|  | Superficial velocity ($cm\, min^{-1}$) | 104 | 104 | 104 |
|  | Mean residence time (min) | 0.07 | 0.144 | 0.072 |
|  | Weight hourly space velocity ($cm^3\, gcat^{-1}\, h^{-1}$) | — | — | 4531 |
| Second reaction region unit | Reaction temperature (° C.) | 856~1015 | 828~983 | 760~1003 |
|  | Reaction pressure(bar) | 1 | 1 | 1 |
|  | $H_2$ addition ($cm^3\, min^{-1}$) | 40 | 40 | 40 |
|  | Superficial velocity ($cm\, min^{-1}$) | 877 | 877 | 877 |
|  | Mean residence time (min) | 0.046 | 0.011 | 0.046 |
|  | Weight hourly space velocity ($cm^3\, gcat^{-1}\, h^{-1}$) | 4434 | 17736 | 4434 |

TABLE 2

|  | Classification | Example 1 | Example 2 | Example 3 |
|---|---|---|---|---|
| Methane conversion (%) |  | 5.8 | 6.0 | 3.5 |
| Molar carbon selectivity (%) | Ethane | 5.5 | 6.4 | 5.2 |
|  | Ethylene | 60.4 | 59.5 | 59.5 |
|  | Acetylene | 2.9 | 14.1 | 1.3 |
|  | C3~C5 | 1.3 | 3.3 | 1.3 |
|  | Benzene | 4.3 | 9.4 | 2.3 |
|  | Toluene | 0 | 0.4 | 0 |
|  | Naphthalene | 0 | 2.5 | 0 |
|  | Alkyl aromatics | 25.6 | 4.4 | 30.4 |
|  | Coke | 0 | 0 | 0 |

As shown in Table 2, with regard to the compositions of the products produced in the reactors of Examples 1 to 3, 100% of methane was converted into hydrocarbons without forming coke. In the case of Example 2, it was confirmed that the selectivity of ethylene was 59.5% and that aromatic compounds including benzene, toluene, naphthalene, and alkyl aromatic compounds were produced with a selectivity of 16.7%. In the case of Example 1, the mean residence time of the first reaction region unit was reduced and the mean residence time of the second reaction region unit was increased compared to the case of Example 2. Accordingly, it could be confirmed that a larger amount of acetylene was converted into aromatic compounds compared to the case of Example 2. The selectivity of ethylene and the selectivity of aromatic compound were found to be 60.3% and 29.9%, respectively.

Meanwhile, in the case of Example 3, it was confirmed that the selectivity of ethylene was 59.5% and that aromatic compounds including benzene, toluene, naphthalene, and alkyl aromatic compounds were produced with a selectivity of 32.7%. It could be seen that the selectivity of acetylene was 1.3% and that the acetylene conversion rate was high when compared to the measurement result of Example 1. High selectivity of aromatic compounds was exhibited even at a low methane conversion rate. This means that the production velocity of acetylene was increased due to the activation of methane in the catalyst layer of the first reaction region unit. Accordingly, it could be confirmed that the velocity of the production reaction of the aromatic compound could be improved by using the first reaction catalyst of the first reaction region unit and the second reaction region catalyst of the second reaction region unit.

Comparative Examples 1 to 3

The same reactor as in Example 1 was used, except that 0.6 g of Fe@$SiO_2$ was charged in the first reaction region unit and quartz was shaped into a tube (inner diameter: 0.74 mm) and then mounted on the second reaction region unit. Hydrogen was not supplied to the second reaction region unit. The reaction was performed under the conditions shown in the following Table 3, and then the obtained product was measured in the same manner as in Example 1. The composition of the product is shown in Table 4.

TABLE 3

|  | Classification | Comparative Example 1 | Comparative Example 2 | Comparative Example 3 |
|---|---|---|---|---|
| First reaction region unit | Reaction temperature (° C.) | 1050 | 1070 | 1122 |
|  | Reaction pressure (bar) | 1 | 1 | 1 |
|  | Methane-containing feed: 45% (v/v) $CH_4$ + 50% (v/v) $H_2$ ($cm^3 min^{-1}$) | 40 | 80 | 160 |
|  | Superficial velocity ($cm\, min^{-1}$) | 104 | 208 | 416 |
|  | Mean residence time (min) | 0.144 | 0.072 | 0.036 |
|  | Weight hourly space velocity ($cm^3\, gcat^{-1}\, h^{-1}$) | 4000 | 8000 | 16000 |
| Second reaction region unit | Reaction temperature (° C.) | 715~951 | 732~971 | 777~1023 |
|  | Reaction pressure(bar) | 1 | 1 | 1 |
|  | $H_2$ addition ($cm^3\, min^{-1}$) | — | — | — |
|  | Superficial velocity ($cm\, min^{-1}$) | 1568 | 3136 | 6271 |
|  | Mean residence time (min) | 0.006 | 0.003 | 0.002 |
|  | Weight hourly space velocity ($cm^3\, gcat^{-1}\, h^{-1}$) | 2309 | 4618 | 9237 |

TABLE 4

| Classification | | Comparative Example 1 | Comparative Example 2 | Comparative Example 3 |
|---|---|---|---|---|
| Methane conversion (%) | | 5.2 | 4.9 | 5.7 |
| Molar carbon selectivity (%) | Ethane | 4.8 | 3.9 | 2.5 |
| | Ethylene | 58.4 | 52.8 | 40.7 |
| | Acetylene | 26.2 | 32.0 | 45.9 |
| | C3~C5 | 4.1 | 5.2 | 5.5 |
| | Benzene | 4.2 | 4.7 | 4.5 |
| | Toluene | 0.1 | 0.3 | 0.3 |
| | Naphthalene | 2.2 | 1.1 | 0.6 |
| | Alkyl aromatics | 0 | 0 | 0 |
| | Coke | 0 | 0 | 0 |

As shown in Table 4, as for the compositions of the products produced in the reactors of Comparative Examples 1 to 3, coke was not formed, but the acetylene conversion rate was reduced compared to the cases of Examples 1 to 3. Accordingly, it could be confirmed that the selectivity of ethylene and the selectivity of aromatic compounds were reduced.

Comparative Examples 4 to 6

Ethylene and an aromatic compound were manufactured from methane using the same reactor as in Example 1. In Comparative Example 4, a hydrogen supply tube in a second reaction region unit was obtained by shaping a second reaction region catalyst having a compositional ratio of $Ni_{11}Cr_{18}Mo_{2.5}Fe_{66.5}C_{0.08}Mn_{2.0}$ into a tube (inner diameter: 0.74 mm). The five hydrogen supply tubes were mounted at equal intervals in the second reaction region unit of the reactor. The surface area of the second reaction region catalyst to the reactor volume of the second reaction region unit was set to 6.5 cm$^{-1}$. In Comparative Examples 5 and 6, the hydrogen supply tube was obtained using a quartz tube (inner diameter: 0.46 mm) and then mounted instead of the hydrogen supply tube including the second reaction catalyst. The reaction was performed under the conditions shown in the following Table 5, and then the obtained product was measured in the same manner as in Example 1. The composition of the product is shown in Table 6.

TABLE 5

| | Classification | Comparative Example 4 | Comparative Example 5 | Comparative Example 6 |
|---|---|---|---|---|
| First reaction region unit | Reaction temperature (° C.) | 1190 | 1101 | 1110 |
| | Reaction pressure (bar) | 1 | 1 | 1 |
| | Methane-containing feed: 45% (v/v) CH$_4$ + 50% (v/v) H$_2$ (cm$^3$min$^{-1}$) | 40 | 40 | 40 |
| | Superficial velocity (cm min$^{-1}$) | 103 | 104 | 104 |
| | Mean residence time (min) | 0.072 | 0.144 | 0.072 |
| | Weight hourly space velocity (cm$^3$ gcat$^{-1}$ h$^{-1}$) | — | — | — |
| Second reaction region unit | Reaction temperature (° C.) | 836~1091 | 759~1002 | 767~1011 |
| | Reaction pressure (bar) | 1 | 1 | 1 |
| | H$_2$ addition (cm$^3$ min$^{-1}$) | 40 | 40 | 40 |
| | Superficial velocity (cm min$^{-1}$) | 1120 | 3136 | 3136 |
| | Mean residence time (min) | 0.036 | 0.003 | 0.013 |
| | Weight hourly space velocity (cm$^3$ gcat$^{-1}$ h$^{-1}$) | 887 | 4618 | 1155 |

TABLE 6

| Classification | | Comparative Example 4 | Comparative Example 5 | Comparative Example 6 |
|---|---|---|---|---|
| Methane conversion (%) | | 5.6 | 10.2 | 5.5 |
| Molar carbon selectivity (%) | Ethane | 4.6 | 3.3 | 2.5 |
| | Ethylene | 52.8 | 44.5 | 43.8 |
| | Acetylene | 0.1 | 32.8 | 42.4 |
| | C3~C5 | 0.6 | 1.7 | 2.3 |
| | Benzene | 3.0 | 13.1 | 3.9 |
| | Toluene | 0 | 0.2 | 0 |
| | Naphthalene | 0 | 1.9 | 5.1 |
| | Alkyl aromatics | 17.4 | 2.5 | 0 |
| | Coke | 21.5 | 0 | 0 |

As shown in Table 6, in the case of Comparative Example 4, the selectivity of acetylene was reduced to 0.1% but coke was produced with the selectivity of 21.5% compared to Examples 1 to 3. Further, in the cases of Comparative Examples 5 and 7, it could be confirmed that the selectivity of ethylene was low and the acetylene conversion rate was reduced compared to Examples 1 and 2.

Therefore, it could be confirmed that the reactor for non-oxidative direct conversion of methane according to the present invention makes it possible to maximize a catalytic reaction velocity, to minimize the production of coke, and to ensure a high conversion rate of methane and a high yield of ethylene and an aromatic compound when ethylene and the aromatic compound are manufactured.

Although the present invention has been described with reference to the above-described embodiments and the accompanying drawings, different embodiments may be provided within the spirit and scope of the invention. Therefore, the scope of the present invention is defined by the appended claims and equivalents thereof, and is not limited to the specific embodiments described herein.

What is claimed is:

1. A reactor for non-oxidative direct conversion of methane, the reactor comprising:
   an introduction unit for introducing a methane-containing feed;
   a reaction unit for reacting the methane-containing feed introduced through the introduction unit to produce a product containing ethylene and an aromatic compound; and a discharge unit for discharging the product containing the ethylene and the aromatic compound produced in the reaction unit, wherein the reaction unit includes a first reaction region unit, for reacting the methane-containing feed introduced through the introduction unit to produce acetylene, and a second reaction region unit, for hydrogenating the acetylene produced in the first reaction region unit to produce the ethylene and the aromatic compound, and the second reaction region unit is provided with a hydrogen supply tube which is coaxially disposed in the reactor and which is hollow so that hydrogen is supplied through the hydrogen supply tube in the direction of the discharge unit towards the introduction unit, wherein the reactor for non-oxidative direct conversion of methane includes a second reaction region catalyst in a reactor inner circumferential surface or in the hydrogen supply tube of the second reaction region unit.

2. The reactor for non-oxidative direct conversion of methane of claim 1, wherein the second reaction region catalyst includes one or more elements selected from the group consisting of iron, chromium, nickel, molybdenum, and manganese.

3. The reactor for non-oxidative direct conversion of methane of claim 1, wherein a ratio of a mean residence time in the second reaction region unit to a mean residence time in the first reaction region unit in the reactor is 0.01 to 1.5.

4. The reactor for non-oxidative direct conversion of methane of claim 1, wherein a ratio of a superficial velocity in the second reaction region unit to a superficial velocity in the first reaction region unit in the reactor for non-oxidative direct conversion of methane is 1 to 30.

5. The reactor for non-oxidative direct conversion of methane of claim 1, wherein a space velocity of the second reaction region unit is 800 to 20,000 $cm^3$ $gcat^{-1}$ $h^{-1}$.

6. The reactor for non-oxidative direct conversion of methane of claim 1, wherein a reaction is performed at 900 to 2,000° C. under 0.1 to 10 bar in the first reaction region unit.

7. The reactor for non-oxidative direct conversion of methane of claim 1, wherein the hydrogenating is performed at 500 to 1,300° C. under 0.1 to 10 bar in the second reaction region unit.

8. The reactor for non-oxidative direct conversion of methane of claim 1, wherein a reactor inner circumferential surface of the first reaction region unit is coated with a first reaction catalyst containing $Si_xN_yO_z$ (x=1 to 3, y=4 or less, z=2 or less).

9. The reactor for non-oxidative direct conversion of methane of claim 1, wherein a ratio of a surface area of the second reaction region catalyst to a reactor volume of the second reaction region unit is 1 to 10 cm'.

10. A method of manufacturing ethylene and an aromatic compound from methane comprising performing non-oxidative direct conversion of methane in the reactor of claim 1.

* * * * *